US009261492B2

(12) United States Patent
Lee et al.

(10) Patent No.: US 9,261,492 B2
(45) Date of Patent: Feb. 16, 2016

(54) METHOD FOR EVALUATING SEMI-QUANTITATIVELY OF CONCRETE CARBONIZATION AND EVALUATING APPARATUS USING THE SAME

(71) Applicant: KOREA INSTITUTE OF CONSTRUCTION TECHNOLOGY, Goyang-si, Gyeonggi-do (KR)

(72) Inventors: Ho Jae Lee, Seoul (KR); Do Gyeum Kim, Goyang-si (KR)

(73) Assignee: KOREA INSTITUTE OF CONSTRUCTION TECHNOLOGY, Goyang-Si, Gyeonggi-Do (KR)

( * ) Notice: Subject to any disclaimer, the term of this patent is extended or adjusted under 35 U.S.C. 154(b) by 0 days.

(21) Appl. No.: 14/414,525

(22) PCT Filed: Jul. 3, 2013

(86) PCT No.: PCT/KR2013/005913
§ 371 (c)(1),
(2) Date: Jan. 13, 2015

(87) PCT Pub. No.: WO2014/137035
PCT Pub. Date: Sep. 12, 2014

(65) Prior Publication Data
US 2015/0168369 A1    Jun. 18, 2015

(30) Foreign Application Priority Data

Mar. 5, 2013    (KR) .................. 10-2013-0023293

(51) Int. Cl.
*G01N 33/38* (2006.01)
*G01N 23/207* (2006.01)

(52) U.S. Cl.
CPC ............ *G01N 33/383* (2013.01); *G01N 23/207* (2013.01); *Y10T 436/204998* (2015.01)

(58) Field of Classification Search
CPC . G01N 23/207; G01N 23/20; G01N 23/2202; G01N 1/286; G01N 2001/2873; G01N 33/38; G01N 33/383; Y10T 436/204998
See application file for complete search history.

(56) References Cited

FOREIGN PATENT DOCUMENTS

| JP | 2011-226961 | 11/2011 |
| JP | 2011-257212 | 12/2011 |
| KR | 10-2002-0040692 | 5/2002 |

OTHER PUBLICATIONS

Chang, Cheng-Feng et al. "The experimental investigation of concrete carbonation depth." Cement and Concrete Research (2006) 36 1760-1767.*

(Continued)

*Primary Examiner* — Christopher A Hixson
(74) *Attorney, Agent, or Firm* — Kile Park Reed & Houtteman PLLC

(57) ABSTRACT

Provided are a method of semi-quantitatively evaluating concrete carbonation including the steps of a specimen preparing step of preparing a concrete specimen for identifying a degree of carbonation, a carbonation depth measuring step of measuring a carbonation depth of the specimen by a method of promoting carbonation of the specimen using a carbonation promoting tester and applying an indicator, an X-ray diffraction (XRD) analyzing step of qualitatively analyzing components of the specimen by an XRD method after cutting the specimen from a top end to a predetermined depth and crushing the specimen. Thus, the method of the present invention may calculate the exposure time of concrete carbonation by converting the analysis result value of XRD to the result value of TG-DTA.

2 Claims, 14 Drawing Sheets

(56) References Cited

OTHER PUBLICATIONS

Scrivener, K. L. et al. "Quantitative study of Portland cement hydration by X-ray diffraction/Rietveld analysis and independent methods." Cement and Concrete Research (2004) 34 1541-1547.*

Villain, Geraldine et al. "Measurement methods of carbonation profiles in concrete: Thermogravimetry, chemical analysis, and gammadensimetry." Cement and Concrete Research (2007) 37 1182-1192.*

International Search Report for International Application No. PCT/KR2013/005913, dated Nov. 28, 2013.

H. J. Lee et al., "Analysis of Carbonation Properties of NPP Concrete Using Thermogravimetric and X-ray Diffraction Method" Proceedings of the Korea Concrete Institute, May 2012, vol. 24, pp. 243-244.

* cited by examiner

METHOD FOR EVALUATING SEMI-QUANTITATIVELY OF CONCRETE CARBONIZATION AND EVALUATING APPARATUS USING THE SAME

BACKGROUND

The present disclosure relates to civil engineering, and more particularly to a method of semi-quantitatively evaluating concrete carbonation and an apparatus for semi-quantitatively evaluating concrete carbonation using the same.

In general, hardened concrete, as a hydration product of cement, exhibits strong basicity because a large amount of calcium hydroxide ($Ca(OH)_2$; portlandite) is formed.

The calcium hydroxide is under the influence of carbon dioxide in the air from the surface of the concrete to slowly change into calcium carbonate ($CaCO_3$; calcite) and water over time, and during this process, reaction products as illustrated in Table 1 are formed.

TABLE 1

| Concrete Carbonation products | |
|---|---|
| Portland cement hydration product | Carbonation products |
| Calcium hydroxide | Calcite and water |
| Calcium silicate hydrate | Calcite, silica gel and water |
| Calcium aluminate hydrate | Calcite, alumina gel, and water |
| Hydrated fertile phases | Calcite, ferric oxide, alumina gel, and water |
| Ettringite and calcium monosulfoaluminate | Gypsum, alumina gel, and water |

Since calcite is neutral, the pH of the concrete gradually changes from strong alkaline to neutral depending on the degree to which portlandite is changed into calcite. The concrete is gradually carbonated from the surface into which carbon dioxide gas and water may easily penetrate.

This phenomenon is called as carbonation (neutralization) of concrete.

The carbonation phenomenon of concrete results in the corrosion of reinforcement steel in the concrete and the generation of swelling pressure, and thus, the carbonation phenomenon of concrete may cause degradation of durability of a structure, for example, cracks occur in the concrete due to the swelling pressure and degradation rapidly proceeds.

Thus, it is important to identify the carbonation of concrete in terms of the durability of the structure.

Typically, research to analyze the carbonation of concrete has been widely conducted, and typical methods of evaluating carbonation are as follows:

First, there is a method of using an indicator (phenolphthalein).

The indicator is used to identify a concentration of hydrogen ions by measuring acidic and basic levels of a measured material or determining the equivalence point of titration, at which acid and base are neutralized, based on the fact that the color of the indicator changes according to the concentration of hydrogen ions.

As described above, since concrete contains a large amount of portlandite in a hydrate, the concrete normally exhibits strong basicity (pH 12 to 13).

When carbon dioxide in the air acts on the concrete, calcite is formed to reduce portlandite exhibiting strong basicity in the hydrate, and thus, carbonation, which gradually reduces the pH of the concrete, proceeds.

Since the concentration of hydrogen ions in the concrete changes according to the progress of the carbonation, the progress of the carbonation may be determined by the presence of discoloration using the indicator.

Herein, it is general to use a phenolphthalein solution as the indicator.

Second, there is a method by differential thermal gravimetric analysis (TG-DTA).

This is a method of measuring thermal changes in the process of the release of bound water or absorbed water through thermal changes in which the energy absorbed or released when a crystal structure changes during the process of heating or cooling the concrete is converted to calories, wherein the method simultaneously performs differential thermal analysis (DTA) investigating an endothermic or exothermic reaction occurred due to the changes in temperature and thermogravimetry (TG) measuring weight change caused by temperature change.

The differential thermal gravimetric analysis (TG-DTA) is a method with high accuracy. However, since the carbonation proceeds from the surface to the inside of the concrete, the differential thermal gravimetric analysis has disadvantageous in that sampling must be conducted according to the depth of the concrete and test equipment is expensive. Thus, the differential thermal gravimetric analysis is used to complement the measurement results obtained by the indicator method.

Third, there is an X-ray diffraction (XRD) method.

The X-ray diffraction method is a method of analyzing a crystalline material, and in general, the objective thereof is to qualitatively analyze the amounts of portlandite and calcite.

An X-ray spectrometer is used to analyze a crystal structure of a material. When a crystal is irradiated with X-rays, X-rays are reflected from crystal lattice planes, and since a diffraction angle of a selected diffraction line and an intensity of X-rays are unique to each mineral, the X-ray diffraction method may distinguish types of the mineral.

In the method, similar to the differential thermal gravimetric analysis, concrete sampled according to the depth are crushed to be used as samples, and a carbonated portion is measured by comparing peak intensities of the portlandite and calcite.

Since the X-ray diffraction method, as a qualitative analysis method, is used to determine a relative amount of a component, there is a limitation in that the quantitative determination of the component is impossible only by the X-ray diffraction method itself. Thus, the X-ray diffraction method is used as an auxiliary means and is widely used for monitoring changes in results and relatively comparing detected components.

Therefore, in order to more accurately evaluate the carbonation of concrete, the analysis may be performed by using all of the above methods.

However, since this may be very cumbersome and there is no certain correlation between the results, there are difficulties in the evaluation.

SUMMARY

The present disclosure provides a method of semi-quantitatively evaluating concrete carbonation only by using an X-ray diffraction (XRD) method, which may convert analysis result values of the XRD method to result values of differential thermal gravimetric analysis (TG-DTA) and may calculate the exposure time of concrete carbonation, and an apparatus for semi-quantitatively evaluating concrete carbonation using the same.

In accordance with an exemplary embodiment of the present invention, there is provided a method of semi-quantitatively evaluating concrete carbonation including the steps of: a specimen preparing step of preparing a concrete specimen for identifying a degree of carbonation; a carbonation depth measuring step of measuring a carbonation depth of the specimen by a method of promoting carbonation of the specimen using a carbonation promoting tester and applying an indicator; an X-ray diffraction (XRD) analyzing step of qualitatively analyzing components of the specimen by an XRD method after cutting the specimen from a top end to a predetermined depth and crushing the specimen; an a step of converting a first result value A analyzed in the X-ray diffraction analyzing step to a second result value B of a differential thermal gravimetric analysis (TG-DTA) method to quantitatively analyze the components of the specimen; and a b step of calculating exposure time of carbonation C of the specimen based on the converted second result value B.

The plurality of specimens may be prepared in a water-binder ratio range of 0.4 to 0.5 in the specimen preparing step.

The method may further include a specimen curing step of water curing the specimen in a temperature range of 18° C. to 22° C. for 25 days to 30 days, before the carbonation depth measuring step.

The a step may be calculated by Equation 1:

$$B = 1.1784A + 0.8704,$$ [Equation 1]

where A represents the first result value of a ratio of calcite/portlandite, and B represents the second result value of the ratio of calcite/portlandite.

The b step may be calculated by Equation 2:

$$C = 8.62B^{2.89},$$ [Equation 2]

where C represents a period of time (days) during which the specimen is exposed to the carbonation.

The carbonation depth measuring step may be performed using the carbonation promoting tester under conditions including a temperature of 15° C. to 25° C., a humidity of 55% to 65%, and a carbon dioxide concentration of 3% to 7%.

A phenolphthalein solution may be used as the indicator.

The X-ray diffraction analyzing step may be performed under conditions including a scan range 2θ of 5° C. to 60° C., a step size of 0.01° C. to 0.03° C., a scan speed of 0.2 sec/step to 0.4 sec/step, a voltage of 35 kV to 45 kV, and a current of 35 mA to 45 mA.

In accordance with another exemplary embodiment of the present invention, an apparatus for semi-quantitatively evaluating concrete carbonation by using the method of semi-quantitatively evaluating concrete carbonation includes a carbonation depth measurement unit formed to measure a carbonation depth of a concrete specimen prepared for identifying a degree of concrete carbonation by a method of promoting carbonation of the specimen using a carbonation promoting tester and applying an indicator; a cut unit for cutting the specimen from a top end to a predetermined depth and crushing the specimen to analyze components of the specimen; an X-ray diffraction (XRD) analysis unit formed to qualitatively analyze the components of the specimen, which is cut and crushed by the cut unit, by an XRD method; an analysis result output unit for outputting a first result value A by analyzing the components of the specimen using the X-ray diffraction analysis unit; a result value conversion unit for converting the first result value A output by the analysis result output unit to a second result value B of a differential thermal gravimetric analysis (TG-DTA) method; and an exposure time calculation unit for calculating exposure time of carbonation C of the specimen based on the second result value B which is converted by the result value conversion unit.

The analysis result output unit may output a ratio of calcite/portlandite among the components of the specimen as the first result value A.

BRIEF DESCRIPTION OF THE DRAWINGS

Exemplary embodiments can be understood in more detail from the following description taken in conjunction with the accompanying drawings, in which:

FIGS. 1 to 3 are graphs illustrating changes in carbonation depth and exposure time of carbonation of specimens classified according to a water-binder ratio (FIG. 1: paste, FIG. 2: mortar, and FIG. 3: concrete);

DETAILED DESCRIPTION OF EMBODIMENTS

Hereinafter, exemplary embodiments of the present invention will be described in detail with reference to the accompanying drawings.

Figure 1:
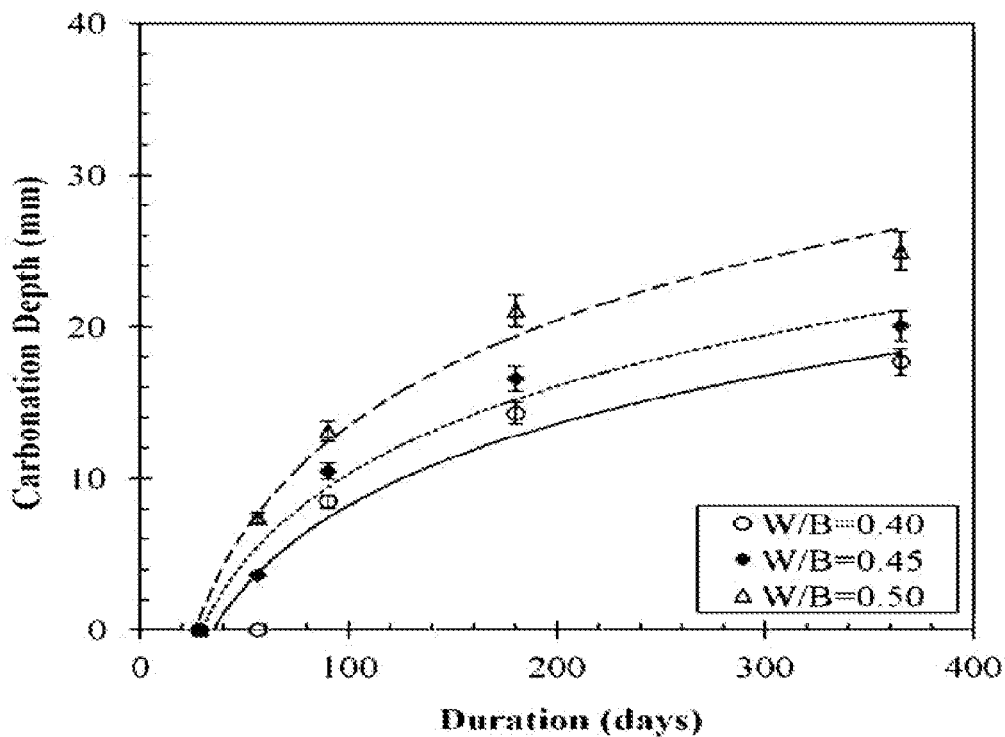
FIG. 1 and other figures herein illustrate results of a verification experiment for verifying a method of semi-quantitatively evaluating concrete carbonation according to the present invention.

As illustrated in FIG. 1 and Table 2 below, a method of semi-quantitatively evaluating concrete carbonation of the present invention includes the steps of: a specimen preparing step of preparing a concrete specimen for identifying a degree of carbonation; a carbonation depth measuring step of measuring a carbonation depth of the specimen by a method of promoting carbonation of the specimen using a carbonation promoting tester and applying an indicator; an X-ray diffraction (XRD) analyzing step of qualitatively analyzing components of the specimen by an XRD method after cutting the specimen from a top end to a predetermined depth and crushing the specimen; an a step of converting a first result value A analyzed in the X-ray diffraction analyzing step to a second result value B of a differential thermal gravimetric analysis (TG-DTA) method to quantitatively analyze the components of the specimen; and a b step of calculating exposure time of carbonation C of the specimen based on the converted second result value B.

That is, the present invention provides a method of semi-quantitatively evaluating carbonation only by using an XRD method in which a result value obtained by qualitatively analyzing components of the specimen by the XRD method is converted to a result value of TG-DTA and the exposure time of concrete carbonation is calculated based on the converted value.

Typically, since the quantitative determination of the components is impossible only by the X-ray diffraction method as a qualitative method, there is a limitation in that the X-ray diffraction method is used as an auxiliary means. However, since the above limitation is addressed in the present invention, the components of concrete may be semi-quantitatively evaluated only by the X-ray diffraction method.

Also, typically, both the X-ray diffraction method and the differential thermal gravimetric analysis method are used as auxiliary methods of evaluating carbonation. However, since there is no certain correlation between the result values, there are difficulties in the evaluation.

In contrast, the present invention provides a method of evaluating a ratio of calcite/portlandite among the components of the specimen by analyzing the correlation between the results of X-ray diffraction analysis and the results of differential thermal gravimetric analysis, and thus, the method may convert the first result value A analyzed by the X-ray diffraction method to the second result value B of the TG-DTA method.

Accordingly, since a consistent result value that has been unable to be identified from a simple comparison between the results analyzed by the X-ray diffraction method and the differential thermal gravimetric analysis method may be obtained, the reliability of the evaluation results may be improved by more accurately analyzing the components of the concrete.

Also, since the X-ray diffraction method has advantages in that it is most accessible among analysis methods using advanced equipment and is easy to use, the second result value B, which is obtained by the differential thermal gravimetric analysis method, may be easily and simply estimated by using the evaluation method of the present invention without actually using the TG-DTA method.

The evaluation method of the present invention will be described in more detail below.

First, in order to identify the degree of carbonation, the plurality of specimens are prepared in a water-binder ratio range of 0.4 to 0.5 in the concrete specimen preparing step.

This is for analyzing changes in the carbonation depth of concrete according to the different water-binder ratios.

After the preparation, all of the specimens are subjected to water curing in a temperature range of 18° C. to 22° C. for 25 days to 30 days, and it is desirable to measure the carbonation depth after standard curing.

After promoting the carbonation of the prepared specimens, the carbonation depth measuring step is performed using a carbonation promoting tester or a method of applying a phenolphthalein indicator.

In particular, in the case that the carbonation of the specimen is promoted by using the carbonation promoting tester, it is desirable to perform the carbonation under conditions including a temperature of 15° C. to 25° C., a humidity of 55% to 65%, and a carbon dioxide concentration of 3% to 7%.

Also, in order to induce the smooth carbonation of all the specimens, a sufficient distance between the specimens is secured to facilitate the contact between the specimens and gas.

The method of applying the indicator to the specimen is a method of most simply and easily identifying the presence of carbonation.

In general, a phenolphthalein solution is used as the indicator and the presence of color change is determined by spraying the phenolphthalein solution.

When the color of the concrete is not changed, the carbonation has proceeded. When the color of the concrete is changed to red, the carbonation has not proceeded, and thus, the concrete is alkaline.

However, since the method of applying the indicator is a method that depends on pH changes, there is a limitation in that the effect of carbonation may not be identified in the case that the carbonation partially occurs or the carbonation has occurred but the pH is outside the range in which the color of the concrete may be changed by the indicator.

Therefore, in the present invention, the carbonation depth measuring step by the typical indicator method through carbonation promoting test as well as the carbonation measuring step through microstructural analysis by the X-ray diffraction method are performed.

Accordingly, more accurate and effective analysis results may be obtained.

In the carbonation depth measuring step, the carbonation depth may be separately measured according to the exposure time of carbonation, and for this purpose, the plurality of specimens having the same water-binder ratio are prepared in the specimen preparing step.

Next, the specimen is cut to a depth of about 10 mm from the top end and crushed, and the X-ray diffraction analyzing step of qualitatively analyzing components is then performed.

It is more effective that the X-ray diffraction analyzing step is performed under conditions including a scan range 2θ of 5° C. to 60° C., a step size of 0.01° C. to 0.03° C., a scan speed of 0.2 sec/step to 0.4 sec/step, a voltage of 35 kV to 45 kV, and a current of 35 mA to 45 mA.

Next, in the present invention, the a step, which is calculated by Equation 1, i.e., $B=1.1784A+0.8704$, is performed to convert the first result value A analyzed in the X-ray diffraction analyzing step to the second result value B of the TG-DTA method.

Herein, A represents the first result value of the ratio of calcite/portlandite among the components of the specimen, and B represents the second result value of the ratio of calcite/portlandite.

In the carbonation process, the dehydration and decomposition of a C—S—H gel are performed in a wide temperature range of 110° C. to 1,000° C., and the decomposition of portlandite is performed in a temperature range of room temperature to 110° C.

In the present invention, the carbonation is evaluated by analyzing changes in the composition of calcite and portlandite in the above temperature range.

Since the above method is the most accurate material analysis method representing the effect of the carbonation and is a widely used method, the changes of two components are only used and relatively compared in the present invention.

In particular, the reason for analyzing the first result value A and the second result value B by representing them as the ratio of calcite/portlandite is that it is a form that best represents trends on the decrease of portlandite and the increase of calcite based on observation in which the carbonation process is related to the above process caused by the combination of portlandite and carbon dioxide.

Next, the b step is performed in which the second result value B converted in the step a is calculated by Equation 2, i.e., $C=8.62B^{2.89}$.

The result value C calculated by Equation 2 represents a period of time (days) during which the specimen is exposed to the carbonation.

That is, the present invention provides a method of calculating the period of time during which the specimen is exposed to the carbonation using Equations 1 and 2 only by the X-ray diffraction method.

Accordingly, the semi-quantitative evaluation of concrete carbonation may be performed only by using the X-ray diffraction method which has limitations in that result values are non-quantitatively obtained.

The present invention also provides an apparatus for semi-quantitatively evaluating concrete carbonation using the evaluation method having the above-described configuration.

First, a carbonation depth measurement unit is formed so as to measure a carbonation depth by promoting carbonation of a concrete specimen prepared for identifying a degree of concrete carbonation and using a carbonation promoting tester or a method of applying an indicator.

In order to analyze components of the specimen, a cut unit for cutting the specimen from a top end to a predetermined depth and crushing the specimen is formed.

An X-ray diffraction (XRD) analysis unit is formed so as to qualitatively analyze the components of the specimen, which is cut and crushed by the cut unit, by an XRD method.

Also, an analysis result output unit for outputting a first result value A by analyzing the components of the specimen using the X-ray diffraction analysis unit, and a result value conversion unit for converting the first result value A output by the analysis result output unit to a second result value B of a differential thermal gravimetric analysis (TG-DTA) method are formed.

An exposure time calculation unit for calculating exposure time of carbonation C of the specimen based on the second result value B, which is converted by the result value conversion unit, is formed.

In particular, the analysis result output unit is configured to output the ratio of calcite/portlandite among the components of the specimen as the first result value A.

Hereinafter, experimental examples for explaining the effect of the present invention will be described.

Table 2 presents component compositions of binders used in the concrete specimen preparing step for identifying the degree of carbonation by the evaluation method of the present invention.

TABLE 2

Result of Analysis for the Components of Binders Used

| Components | OPC | FA |
|---|---|---|
| $SiO_2$ | 20.10 | 54.70 |
| $Al_2O_3$ | 5.22 | 24.80 |
| $Fe_2O_3$ | 2.76 | 8.76 |
| CaO | 55.90 | 2.99 |
| MgO | 2.97 | 1.15 |
| $SO_3$ | 1.87 | 0.32 |
| LOI | 1.56 | 3.56 |

As illustrated in Table 2, there were no difference between the components of the binders and those of Type 1 Portland cement.

Also, with respect to the specimens of the present invention, paste and mortar specimens were prepared as cubic specimens having a size of 50 mm×50 mm×50 mm in accordance with ASTM C 109, and concrete specimens were prepared as cylindrical specimens having a size of 100 mm×200 mm.

All of the specimens used in a verification experiment of the present invention were prepared by substituting with fly ash (FA) in an amount of 20% of the weight of cement (OPC: Ordinary Portland Cement).

As described above, the paste, mortar, and concrete specimens each having different water-binder ratios of 0.4, 0.45, and 0.5 were prepared in order to analyze the changes in the carbonation depth according to the water-binder ratio.

Also, the plurality of specimens having the same water-binder ratio were further prepared and analyzed in order to analyze chemical changes of the specimens according to the exposure time of carbonation, and after promoting the carbonation of the specimens, carbonation depths for each specimen were measured after 28 days, 56 days, 91 days, 180 days, and 365 days.

After the preparation of the specimens, in order to promote the carbonation, all of the specimens were subjected to water curing in a temperature range of 18° C. to 22° C. for about 28 days before being exposed to carbon dioxide, and the effect of the carbonation after standard curing was examined.

In the case that a carbonation promoting tester was used in the carbonation depth measuring step, the carbonation promoting tester was used under conditions including a temperature of 20° C., a humidity of 60%, and a carbon dioxide concentration of 5%, and carbonation depths were measured at a curing time of 28 days, 56 days, 91 days, 180 days, and 365 days.

Also, in order to minimize the effect due to aggregates during the analysis, the paste specimens were used to measure the changes in the carbonation depth.

In the case in which the carbonation depth was measured by the indicator method, the specimens were taken out from a carbonation chamber on each experimental date and were fractured with a universal testing machine.

A phenolphthalein solution, which was prepared by dissolving a 1% phenolphthalein solution in 99% ethanol and adding distilled water thereto, was sprayed on the surface of the fractured specimens.

Phenolphthalein changes color in a pH range of 8.3 to 9.5, and Table 3 presents different pH ranges of pH indicators.

TABLE 3 pH indication value of several indicators

| Indicator | pH range |
|---|---|
| Tropaeolin O | pH 11.1-12.7 |
| Alizarin yellow R | pH 10.2-12.2 |
| Thymolphthalein | pH 9.3-10.5 |
| Phenolphtalein | pH 8.3-9.5 |

In order to conduct more accurate and effective analysis, it may be desirable to measure a carbonation depth by performing core sampling if possible or by spaying the phenolphthalein solution on a cutting surface in the field immediately after exposure when the specimen was exposed in the air for the measurement of the carbonation depth during the experiment.

In the present verification experiment, carbonation was measured by cutting the center of the specimen, the cutting of the specimen was performed by using a fret saw in order to minimize an additional carbonation effect that may occur due to frictional heat between a cutter and the specimen, and a method of crushing the specimen from the surface along the cutting surface using a stainless medicine pestle was used.

The depths of carbonated portions were divided into a maximum depth, a minimum depth, and an average depth, and were measured using a vernier calipers.

Also, each of the plurality of specimens was measured according to the exposure time of carbonation and average values thus obtained were used.

Next, the components of the cut and crushed specimens were analyzed by the differential thermal gravimetric analysis (TG-DTA) method in order to verify a step of converting the first result value A analyzed in the X-ray diffraction analyzing step of the present invention to the second result value B of the TG-DTA method and the b step of calculating the exposure time of carbonation C based on the converted second result value B.

In general, with respect to the differential thermal gravimetric analysis method, calcite, as a typical material in carbonated concrete, is decomposed in a temperature range of 600° C. to 900° C., and portlandite is decomposed in a temperature range of 400° C. to 500° C.

The analysis was carried out with a TG/DTA 7300 instrument by Seico Inst., and was performed using carbon dioxide free nitrogen under conditions including a temperature range of room temperature to 1,200° C., a heating rate of 10° C./min, and a flow rate of 10 ml/min.

Changes in the value of each material at a specific temperature were identified from the analysis results, and the transition temperature range of each main material in the concrete was determined with reference to temperature ranges presented in Table 4.

TABLE 4

Temperature Ranges of Composition

| Compounds | Temperature Ranges |
|---|---|
| Gypsum | 180° C. |
| Ettringite | 250-290° C. |
| Portlandite | 400-450° C. |
| Calcite | 600-900° C. |

The components of the cut and crushed specimens were analyzed by the XRD method.

The analysis was carried out with a D8 Foxus instrument by Bruker AXS, and was performed under conditions including a scan range 2θ of 5° C. to 60° C., a step size of 0.02° C., a scan speed of 0.3 sec/step, a voltage of 40 kV, and a current of 40 mA.

The analysis results were identified from peak values corresponding to crystals using the Joint Committee on Powder Diffraction Standards (JCPDS) cards.

Table 5 presents JCPDS card numbers for identifying the results by the X-ray diffraction method.

TABLE 5

Compounds and JCPDS No. for XRD method

| Compounds | Chemical Formula | JCPDS Card No. |
|---|---|---|
| Calcium Carbonate Vaterite, syn | $\mu\text{-}CaCO_3$ | 025-0127 |
| Calcium Carbnoate Calcite, syn | $CaCO_3$ | 005-0586 |
| Calcium Hydroxide Portalndite, syn | $Ca(OH)_2$ | 004-0733 |
| Calcium Silicate Hydrate | $Ca_{1.5}SiO_{3.5} \cdot xH_2O$ / $1.5CaO \cdot SiO_2 \cdot xH_2O$ | 033-0306 |
| Calcium Silicate Hydrate | $CaO \cdot SiO_2 \cdot H_2O$ | 009-0210 |

The analysis results obtained by the verification experiment will be described below.

First, with respect to the results of carbonation depth measurement, a carbonation depth according to the exposure time of carbonation on each measurement date was obtained by the depth measurement from the surface.

An average value of the results from the plurality of specimens for each formulation on each measurement date was calculated, and the measurement results were expressed as a graph using the value thus obtained. It was confirmed that each measurement value was included with a tolerance of ±10° C. from the average value.

Figure 2:
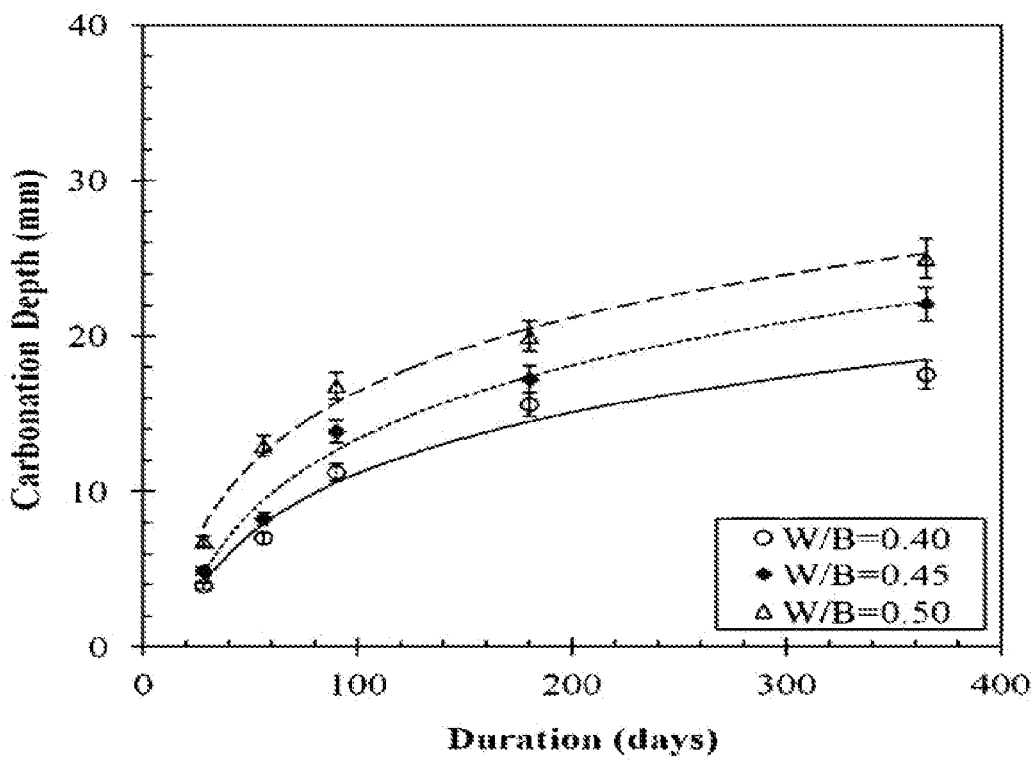
Figure 3:
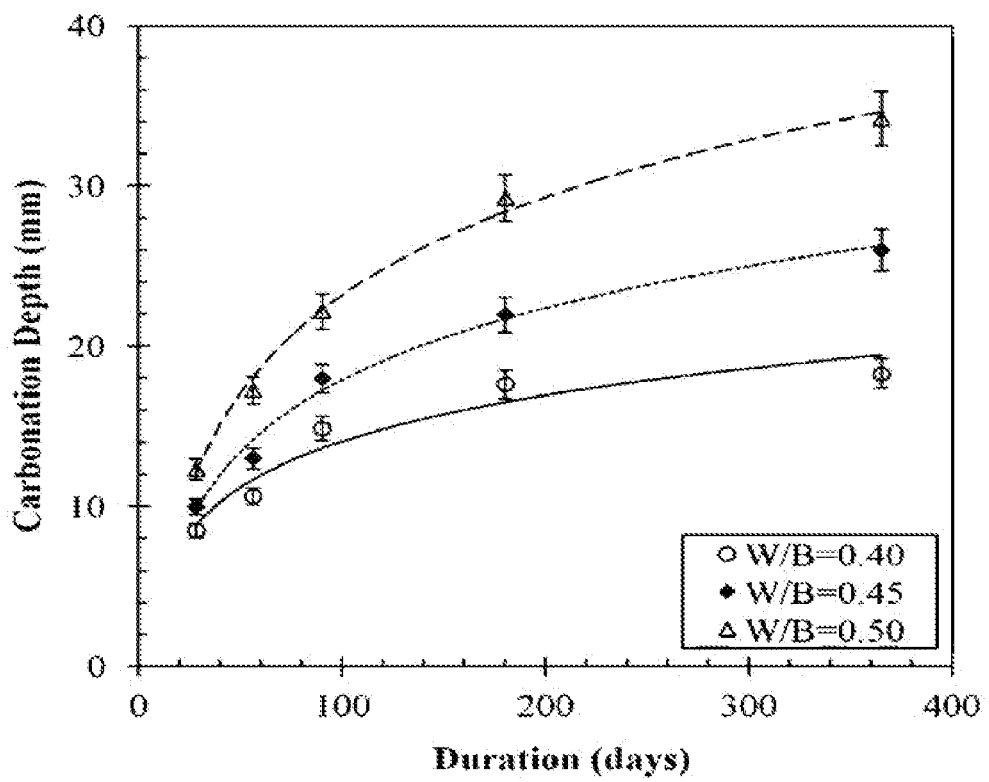

FIGS. 1 to 3 are graphs illustrating changes in the carbonation depth and the exposure time of carbonation of the paste, mortar and concrete specimens classified according to the water-binder ratio.

As a results of analyzing the trend of each measurement result by a log function, the coefficient of determinations ($R^2$) of all formulations were in a range of a minimum of 0.929 to a maximum of 0.994, and thus, all the results were quite reliable.

Also, for each formulation, it may be confirmed that a carbonation rate increased as the water-binder ratio increased.

This was the same tendency as the existing research results in which the carbonation progress rate tended to decrease as the design strength increased.

Figure 4:
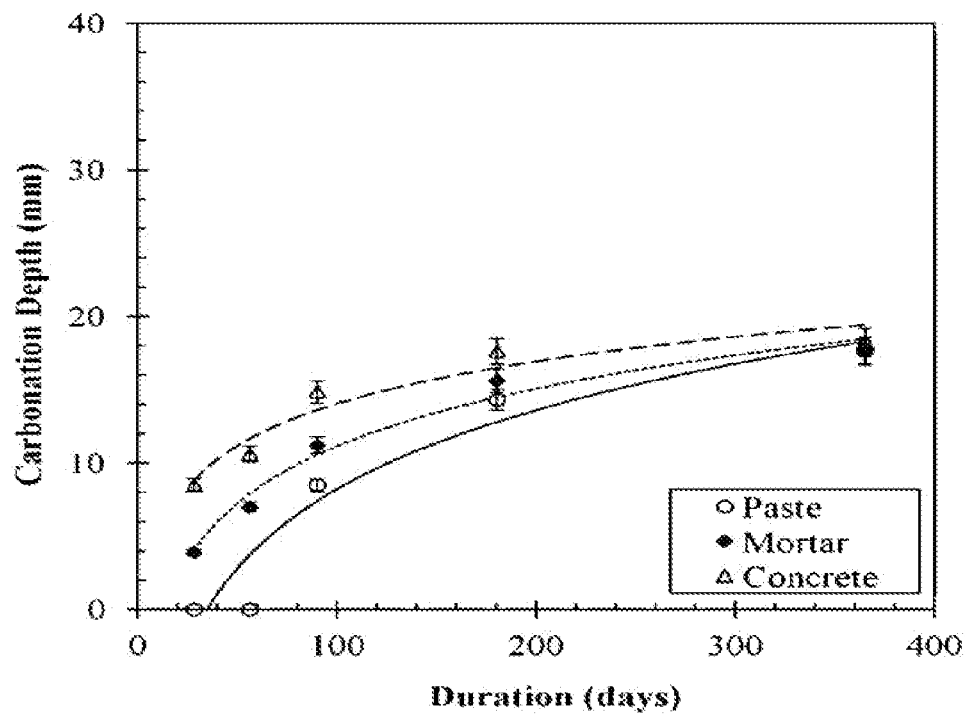
FIGS. 4 to 6 are graphs illustrating changes in carbonation depth according to the exposure time of carbonation of specimens (FIG. 4: W/B=0.40, FIG. 5: W/B=0.45, and FIG. 6: W/B=0.50)
Figure 5:
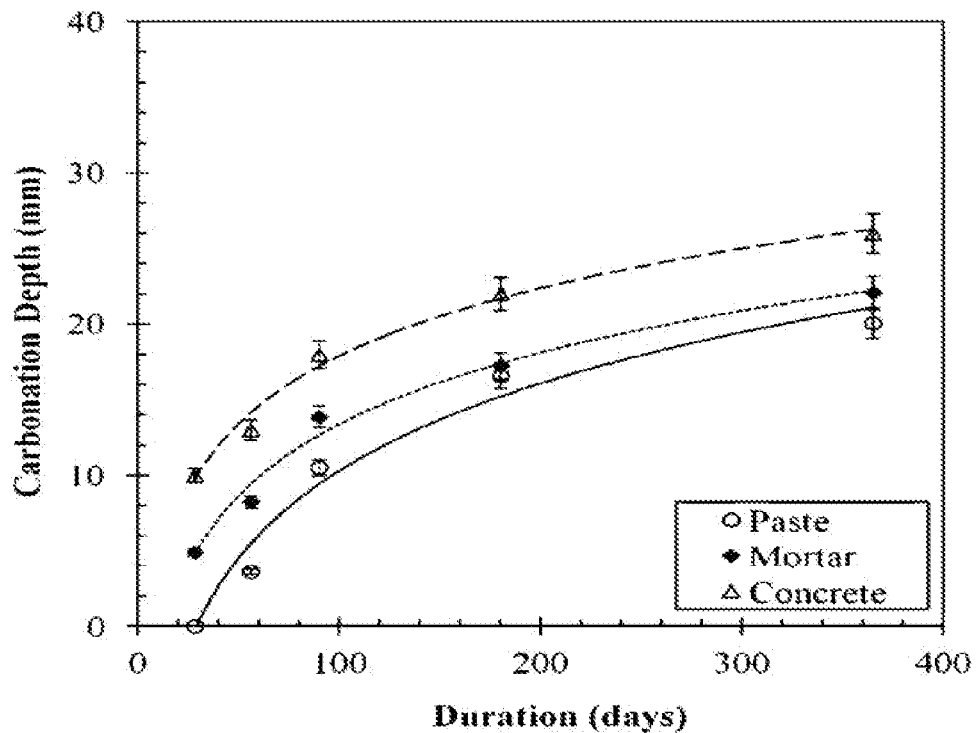
Figure 6:
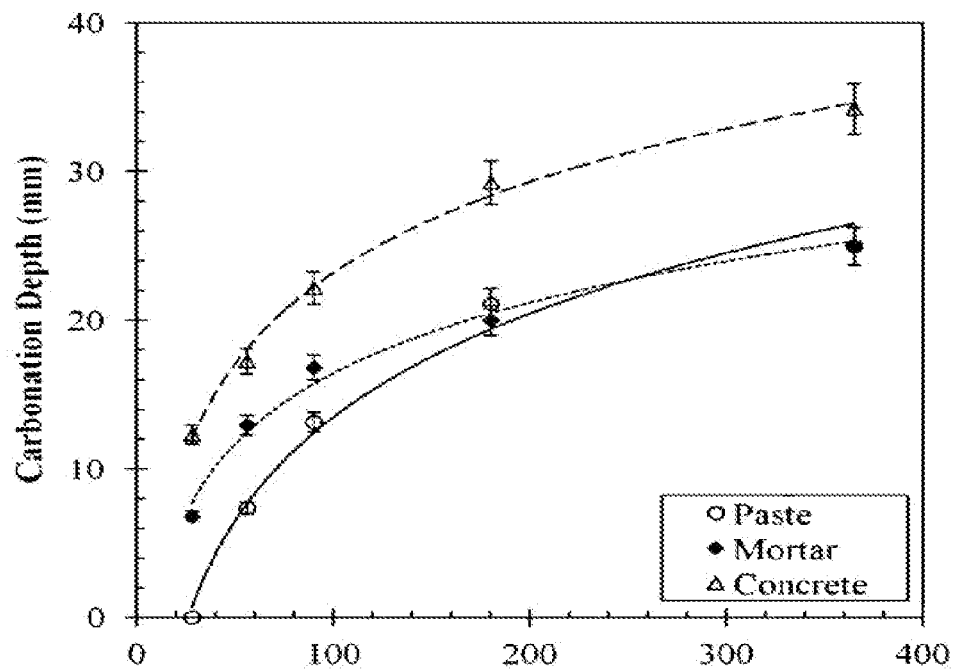

According to the result of analyzing the effect of the aggregates, it may be understood that the degree of carbonation of the concrete was the highest in comparison to those of the paste and the mortar from the results of the carbonation depth measurement of all formulations. However, with respect to the carbonation progress rate, it may be understood that the paste had the fastest carbonation rate as the exposure time of carbonation increased, and this may be confirmed from the graph of the carbonation depth according to the water-binder ratio as illustrated in FIGS. 4 to 6.

As a result of analyzing the trend of each formulation using a log scale, a carbonation depth of the paste was in a range of 7.78 to 8.83 according to the water-binder ratio, and thus, if a continuous carbonation experiment was performed after 365 days, it is estimated that the carbonation occurs in the carbonation depth sequence of the paste, the mortar, and the concrete.

It may be considered that the above result was due to the fact that initial carbonation rapidly occurred because, during the initial carbonation, carbonate ions easily penetrated through an inter transition zone between concrete surface aggregates and cement paste and capillary pores formed due to the effect of bleeding.

However, since the presence of the aggregates may prevent the penetration of the carbonate ions as the carbonate ions moved into a cement paste matrix when the exposure time of carbonation increased, it was considered that, with respect to the concrete, the rate was gradually decreased.

Next, the result according to the differential thermal gravimetric analysis method was analyzed with reference to Table 6.

Table 6 presents the results of differential thermal gravimetric analyses to date which are summarized by Hacelbach.

TABLE 6

Temperature Ranges in Various Studies (° C.) [9]

| Author | Ca(OH)$_2$ TGA decomposition | CaCO$_3$ TGA Decomposition |
|---|---|---|
| Chang and Chen (2006) [10] | 425-550 | 550-950 |
| Papadakis et al. (1992) [11] | 460 | |
| Papadakis et al. (1991) [12] | 400-500 | 600-800 |
| Huntzinger (2006) [13] | 300-500 | 500-800 |
| Huijgen et al. (2005) - slag [14] | | >500 |
| Taylor et al. (1985a, b) [15, 16] | 450-650 | |
| Ramachandran et al. (1964) [17] | 464(DTA) | 850-950 calcite |
| Cole and Kroone (1960) [18] | | 600-750 poorly crystallized 820 well crystallized |
| Stern (2001) [19] | | 827-927 calcite |

As illustrated in Table 6, with respect to the transition temperature range of each main material in concrete, it is considered that the dehydration and decomposition of portlandite and calcite mainly occur in a temperature range of about 300° C. to 650° C. and 500° C. to 950° C., respectively.

The results of analyzing a weight reduced by the dehydration and decomposition occurred in the above temperature range have been widely used as a quantitative method that may calculate an amount of moles of a crystalline material and have also been used for verifying other analysis results.

Changes in portlandite, in which the decomposition occurs in the above temperature range during the process of performing analysis using the differential thermal gravimetric analysis method, are represented by Equation 3 below.

[Equation 3]

Also, a process in which carbon dioxide is decomposed from calcite, is represented by Equation 4 below.

[Equation 4]

In order to perform component analysis by the differential thermal gravimetric analysis method in the verification experiment of the present invention, samples having a length of 10 mm were taken from the surface portion of the specimen and the degree of carbonation was analyzed according to the exposure time of carbonation.

Figure 7:
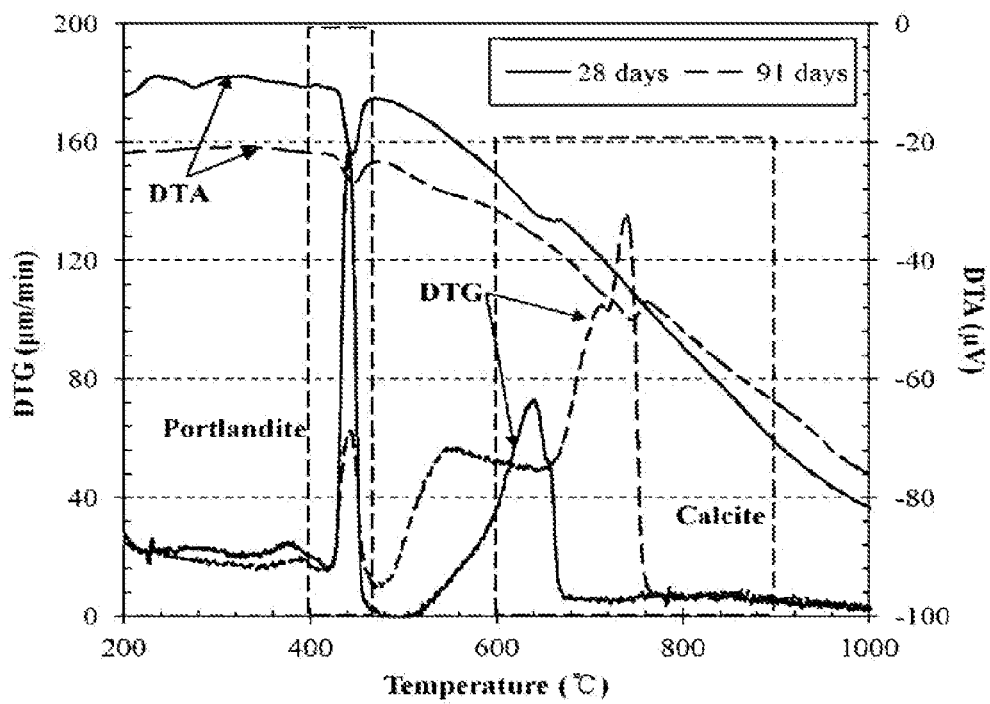
FIG. 7 is a graph illustrating variations of differential thermal analysis (DTA) and differential thermogravimetry (DTG) of specimens according to time after carbonation promotion.

FIG. 7 is a graph illustrating the results obtained by differential thermal analysis (DTA) and differential thermogravimetry (DTG) of the specimens respectively measured after the exposure time of carbonation of 28 days and 91 days.

In the above analysis, the temperature range was referred on the basis of the existing research results illustrated in Table 6, and a range of portlandite was set to a temperature range of 400° C. to 450° C., in which the greatest change occurred in the graph, and a range of calcite was set to a temperature range of 600° C. to 900° C.

As can be seen clearly in the result measured after 28 days and 91 days after the carbonation promotion in the graph illustrated in FIG. 7, the DTA result of the portlandite measured after 28 days was about 150 μg/min and the DTA result measured after 91 days was about 60 μg/min. Thus, it may be confirmed that the DTA result of the portlandite was decreased by more than half.

In contrast, the DTG result after 28 days was about 70 μg/min and the DTG result after 91 days was about 140 μg/min. Thus, it may be confirmed that the DTG result was increased by approximately two times.

In particular, there were changes in DTA values in the portlandite and calcite ranges, and in the case of after 28 days, it may be confirmed that there was a large amount of change in the portlandite range, but a small amount of change was detected in the calcite range.

Also, according to the analysis results thus measured by the DTA and DTG methods, result values measured by TG were analyzed on the basis of a temperature range of portlandite of 400° C. to 450° C. and a temperature range of calcite of 600° C. to 900° C.

Figure 8:
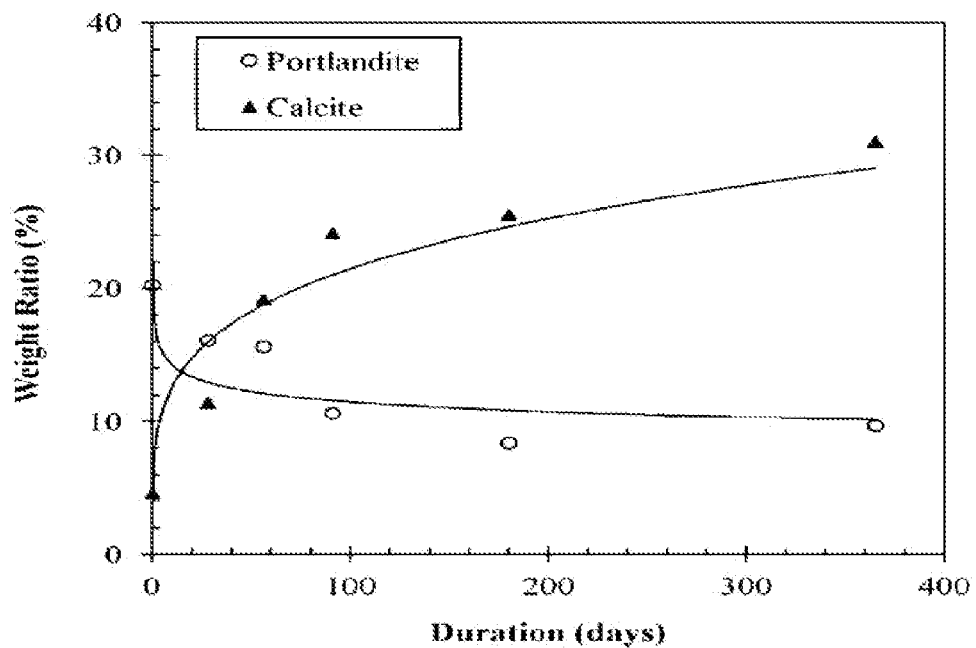
FIGS. 8 to 10 are graphs illustrating changes in portlandite and calcite which are analyzed by a thermal gravimetric analysis method (FIG. 8: W/B=0.40, FIG. 9: W/B=0.45, and FIG. 10: W/B=0.50)
Figure 9:
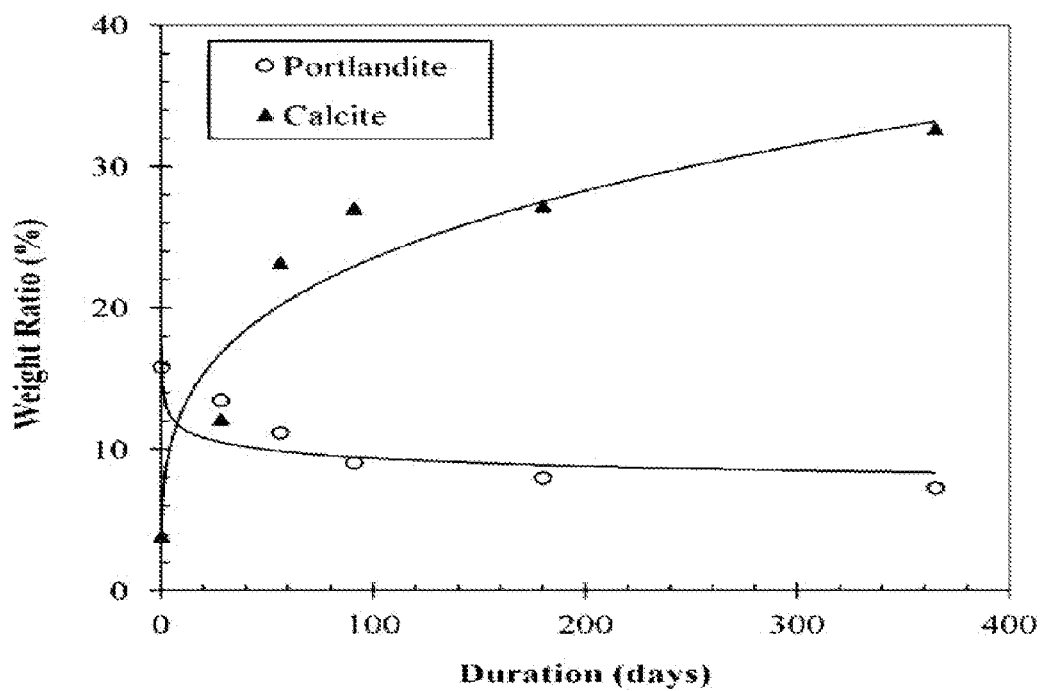
Figure 10:
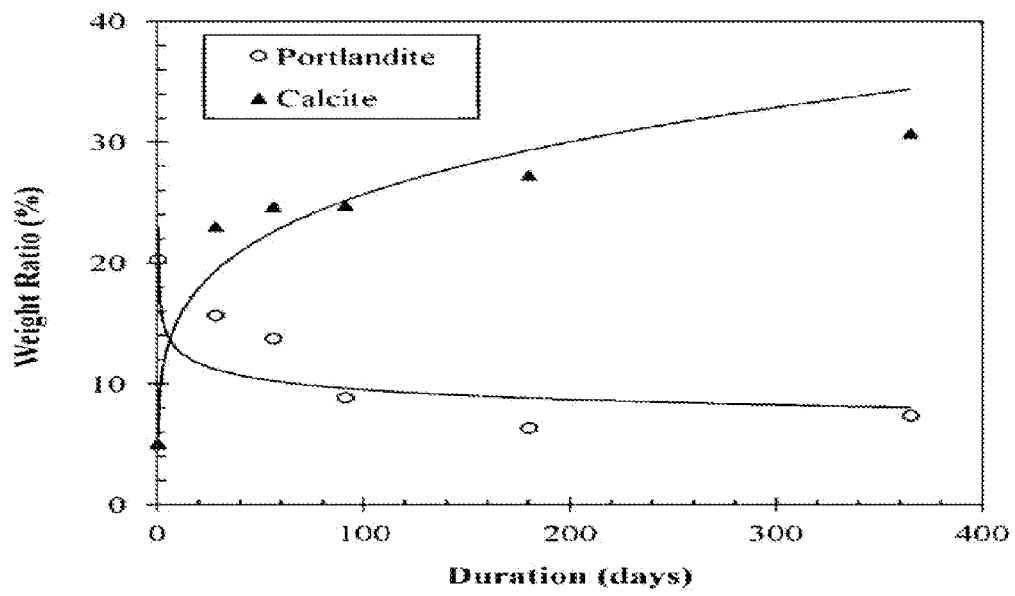

FIGS. 8 to 10 are graphs illustrating contents of components with respect to a total weight of the specimen in which an amount of moles of each component decomposed in each range was measured through the result values obtained by TG and the total weight of the specimen was converted to 100.

According to the graphs illustrated in FIGS. 8 to 10, the result of analyzing the component, in a state in which the specimen was not degraded from 0 days to immediately after 28 days of the water curing, was used as an indicator for determining the degradation.

As a result of calculating the amounts of portlandite and calcite, an initial amount of the calcite included was in a range of 3.9 wt % to 5.1 wt %, and an initial amount of the portlandite included was in a range of 15.8 wt % to 20.3 wt %.

Also, the amount of the calcite was compared with the research result by Dweck et al. in which the content of calcite was analyzed by a TG-DTA method using a cement paste.

In the above research, as a result of analyzing the cement paste that was water cured for 28 days after the preparation of a specimen, the amount of calcite included was about 20%.

That is, it was confirmed that the above result was similar to the analysis result obtained by performing the present study.

Next, the results obtained through analyzing the specimens by the XRD method will be described.

In the verification experiment of the present invention, the specimens, which were analyzed by TG-DTA according to the exposure time of carbonation during the carbonation experiment, were also analyzed by the XRD method, and thus, qualitative comparison was performed together.

Figure 11:
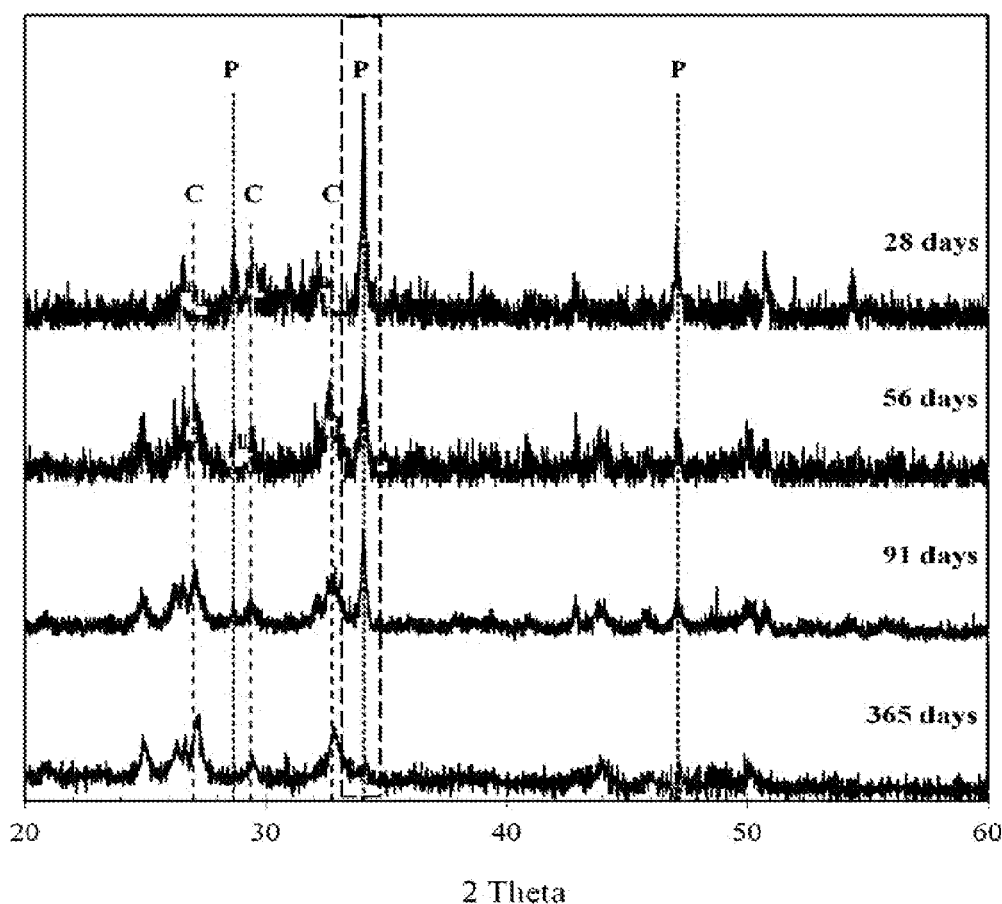
FIGS. 11 and 12 are graphs illustrating changes in XRD analysis results according to the exposure time of carbonation (FIG. 11: changes in XRD analysis results of a paste according to the exposure time of carbonation, and FIG. 12: changes in XRD intensity according to the exposure time of carbonation in a portlandite range)

The results obtained by the XRD method are illustrated in FIG. 11.

FIG. 11 is a graph illustrating changes in the XRD analysis results from an exposure time of carbonation of 28 days to 365 days.

In the graph illustrated in FIG. 11, portions denoted as "P" are portlandite, portions denoted as "C" are calcite, and three peaks for each component shown in the graph were marked by selecting peaks having the greatest amount of change according to the exposure time of carbonation among many peaks that are presented in JCPDS.

Figure 12:
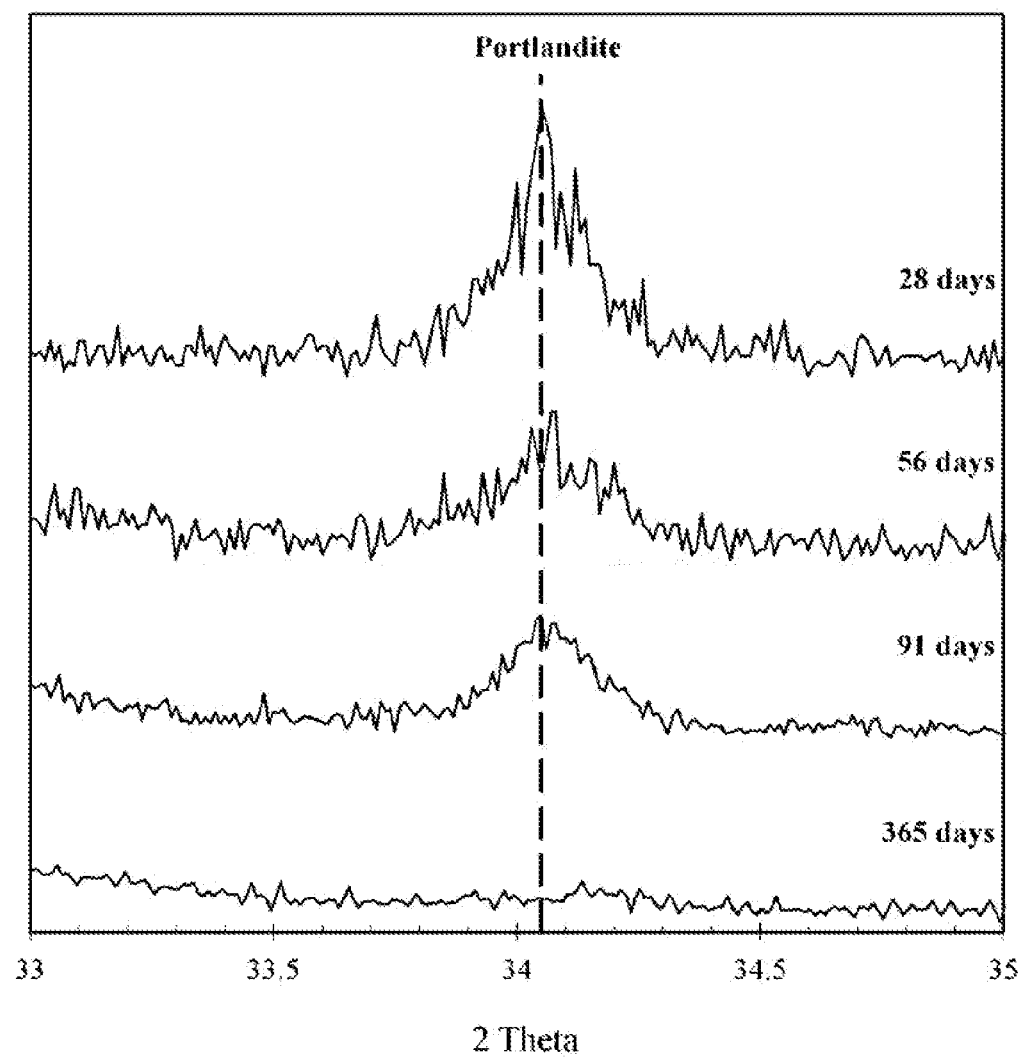

For example, a graph illustrated in FIG. 12 illustrates changes in XRD intensity according to the exposure time of carbonation in the portlandite range.

As illustrated in the graph of FIG. 12, as a result of examining the changes in the intensity at 2θ of portlandite of 34.089° from 28 days to 365 days, it was clearly seen that the intensity tended to decrease. Thus, peaks clearly showing increasing and decreasing tendencies were selected, and their positions are illustrated in FIG. 11.

As a result, it may be clearly confirmed the decreasing tendency of portlandite and the increasing tendency of calcite.

Figure 13:
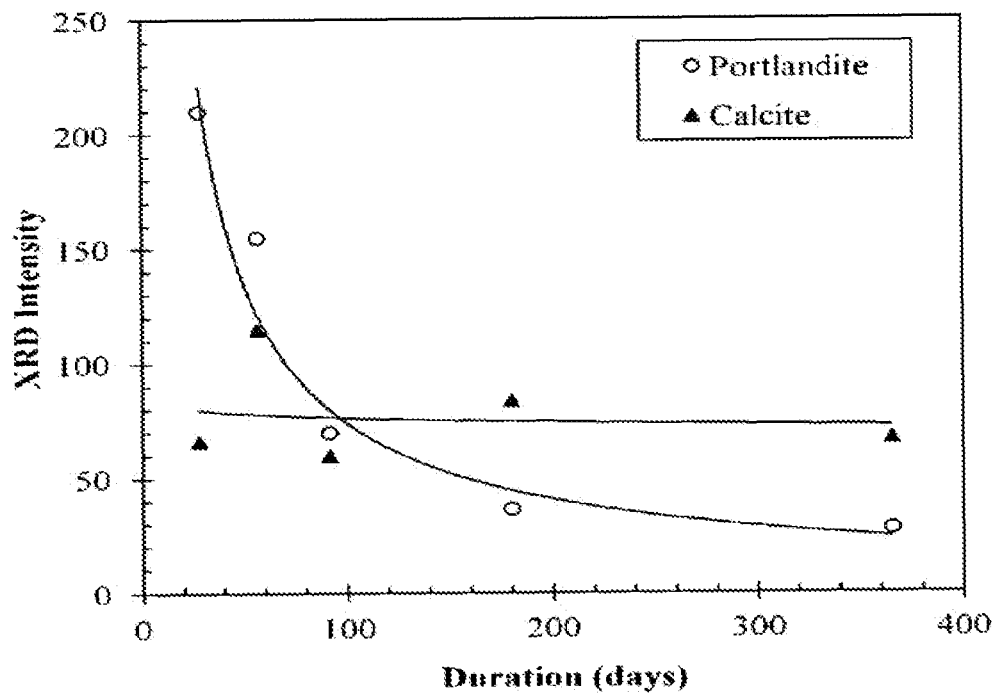
FIGS. 13 to 15 are graphs illustrating qualitative changes in the amounts of portlandite and calcite which are analyzed by XRD intensity analysis (FIG. 13: W/B=0.40, FIG. 14: W/B=0.45, and FIG. 15: W/B=0.50)
Figure 14:
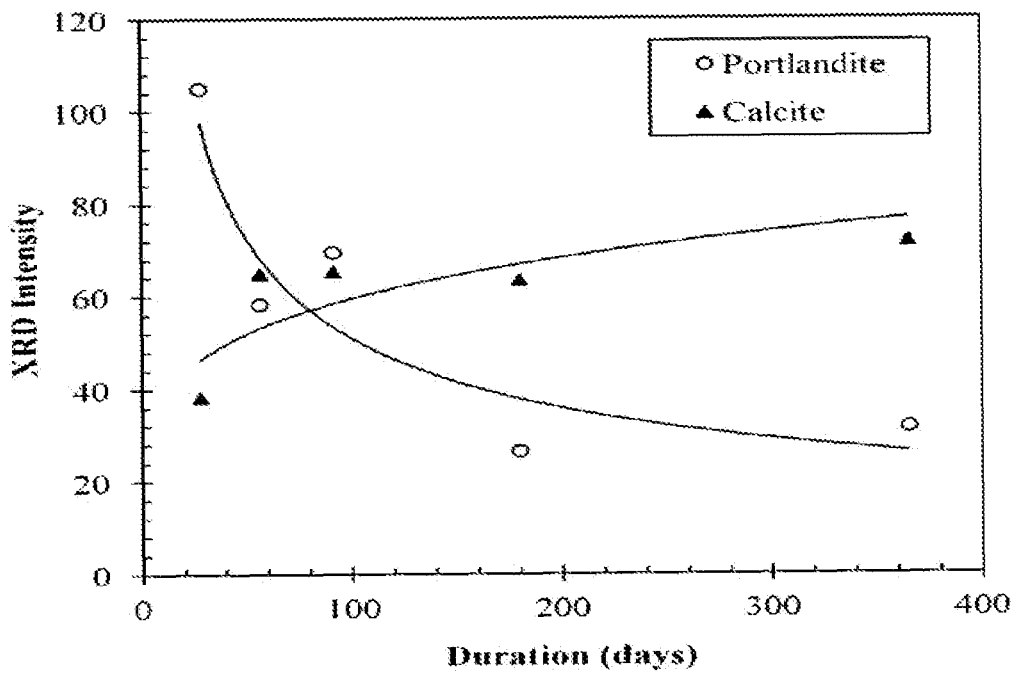
Figure 15:
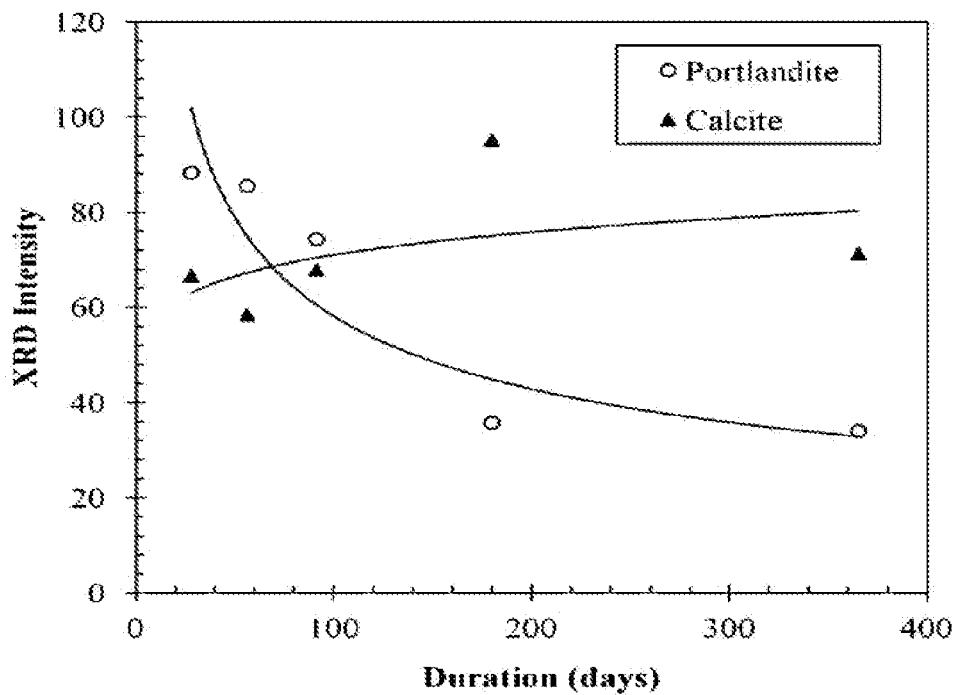

Also, in order to quantitatively express the qualitative changes in the components, intensities of three peaks selected for each component, portlandite at 28.662°, 34.089°, and 47.124, and calcite at 26.998°, 29.406°, and 32.778°, were all combined and their trends are illustrated in FIGS. 13 to 15.

Consequently, accuracy of the analysis results obtained by the XRD method was relatively lower than that of the analysis results obtained by the TG-DTA method that are illustrated in FIGS. 8 to 10. However, the decreasing tendency of portlandite and the increasing tendency of calcite may be confirmed from the graph.

In the verification experiment of the present invention, the dehydration and decomposition of the C—S—H gel were performed in a wide temperature range of 110° C. to 1,000° C., and the decomposition of portlandite was performed in a temperature range of room temperature to 110° C. during the carbonation process. Accordingly, changes in the compositions of two materials, portlandite and calcite, were analyzed in the above temperature ranges.

As illustrated in FIGS. 8 to 10, with respect to the component changes for each water-binder ratio according to the exposure time of carbonation, both the TG-DTA graph and the XRD graph merely illustrate tendencies according to the exposure time due to the effect of carbonation.

Therefore, in order to relatively compare both graphs, the amounts of portlandite and calcite were represented as portlandite/calcite in the present invention.

FIGS. 16 to 19 are graphs illustrating changes in calcite/portlandite according to the exposure time which are analyzed by the differential thermal gravimetric analysis method.

As illustrated in the graphs, a high coefficient of determination ($R^2$) ranging from 0.90 to 0.97 was obtained in the case of the differential thermal gravimetric analysis method, and thus, it may be understood that the reliability of the tendency was considerably high.

Figure 16:
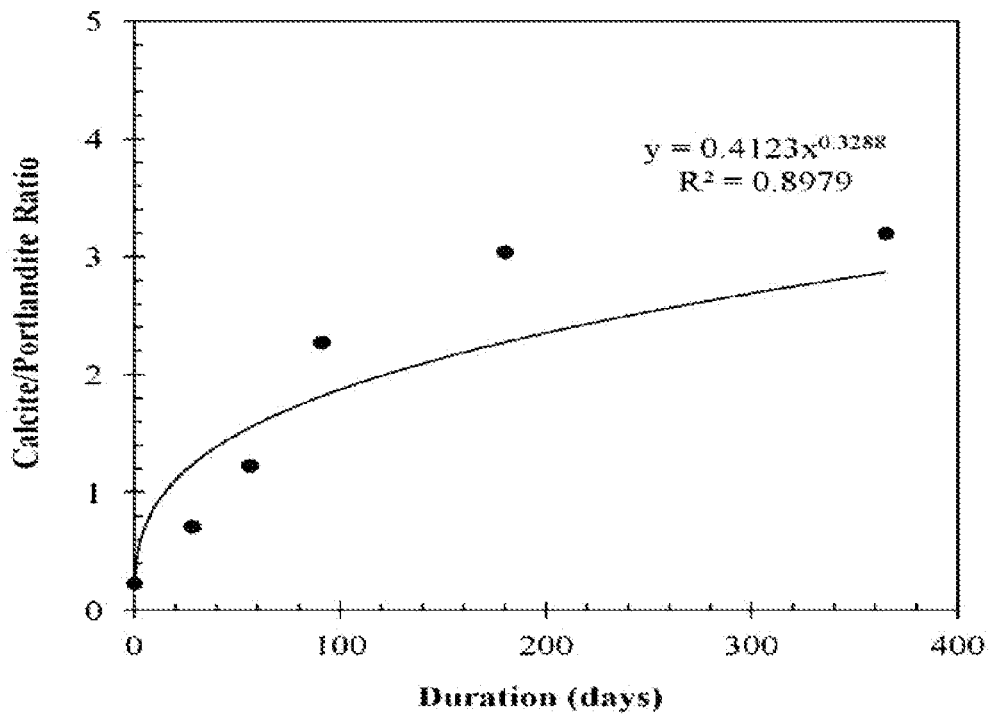
FIGS. 16 to 18 are graphs illustrating changes in calcite/portlandite ratio according to the exposure time which are analyzed by TG-DTA (FIG. 16: W/B=0.40, FIG. 17: W/B=0.45, and FIG. 18: W/B=0.50)
Figure 17:
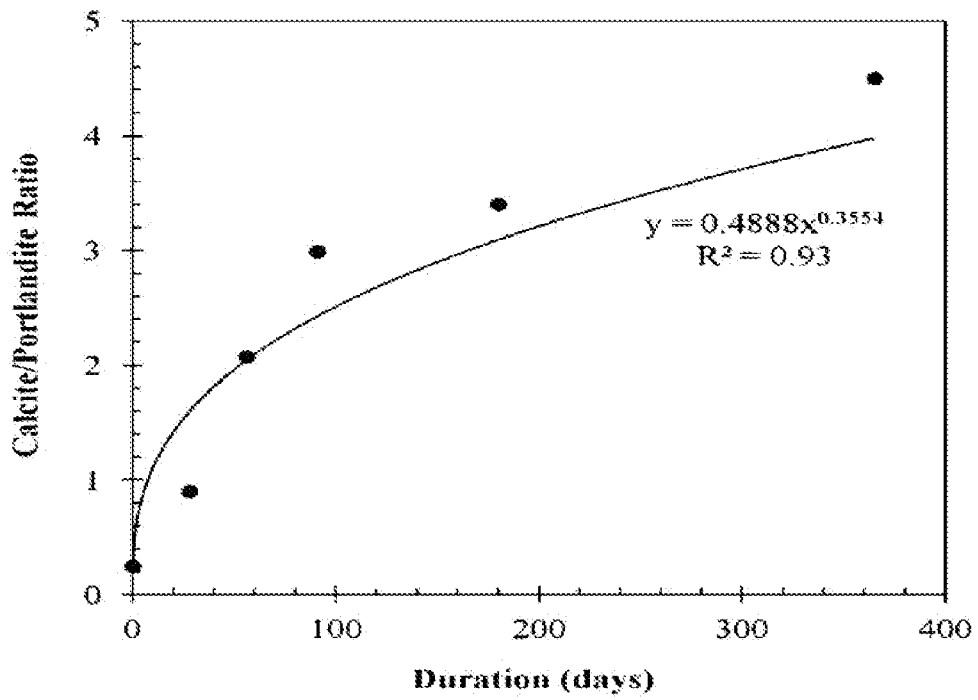
Figure 18:
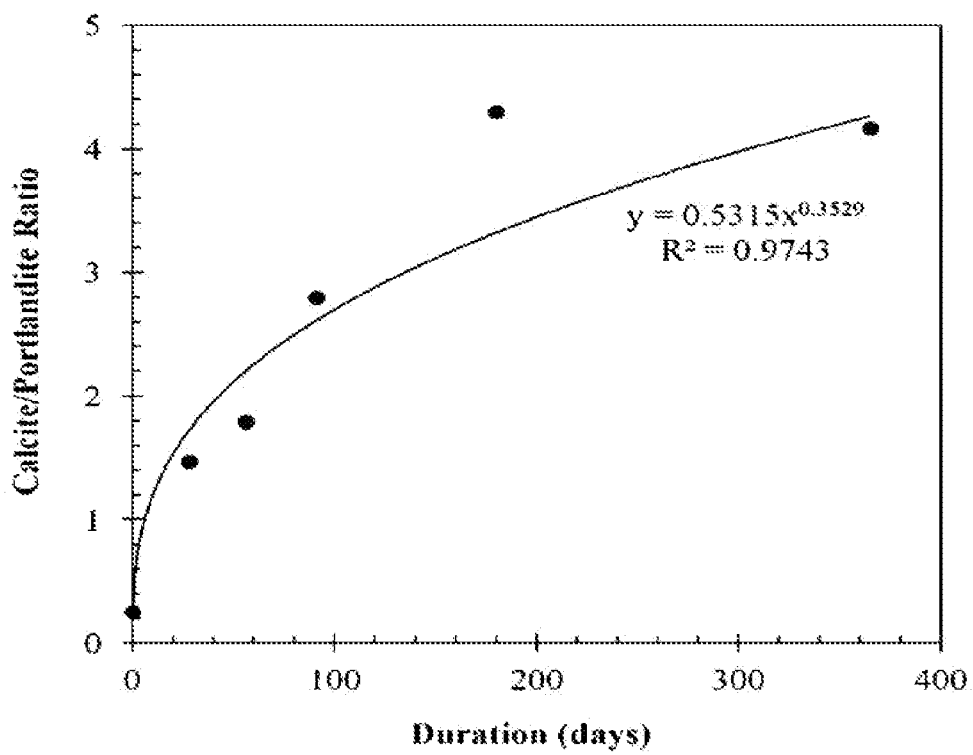
Figure 19:
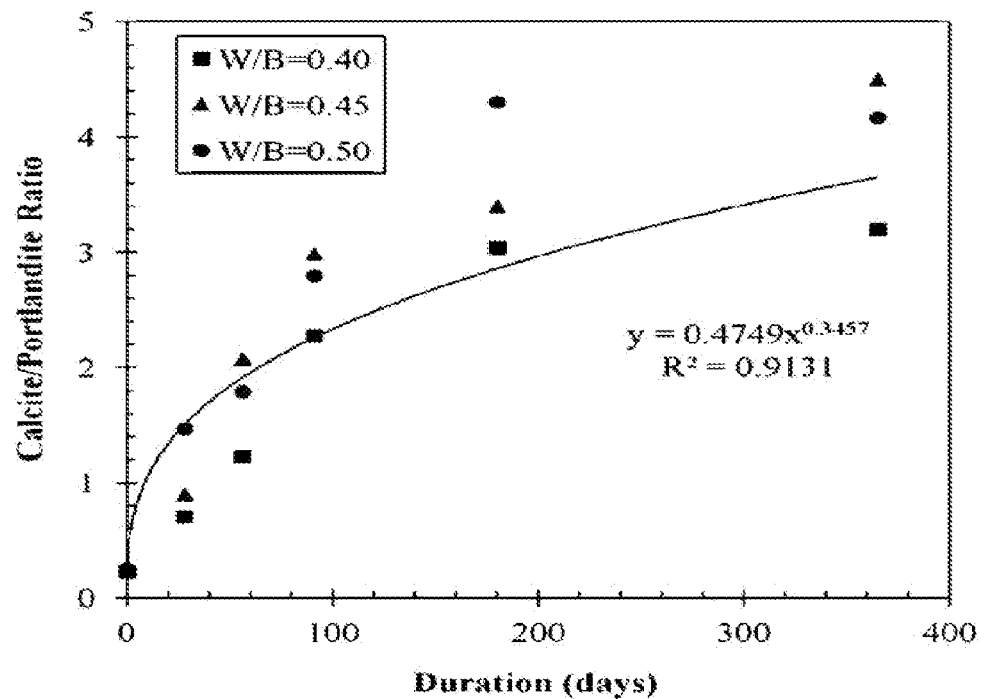
FIG. 19 is a graph collectively illustrating data of FIGS. 16 to 18.

Also, as a result of illustrating three graphs in FIG. 19 in order to relatively compare each graph illustrated in FIGS. 16 to 18, it may be understood that the higher the water-binder ratio was, the higher the rate of increasing the calcite/portlandite ratio was, and it may be confirmed that the result exhibited a constant tendency according to the cueing time although there was a difference according to the water-binder ratio.

The tendency was similar to the tendency of the graph showing the changes in carbonation depth according to the exposure time of carbonation, and it is considered that the carbonation rate at the same depth according to the measurement time may also be estimated thereby.

Figure 20:
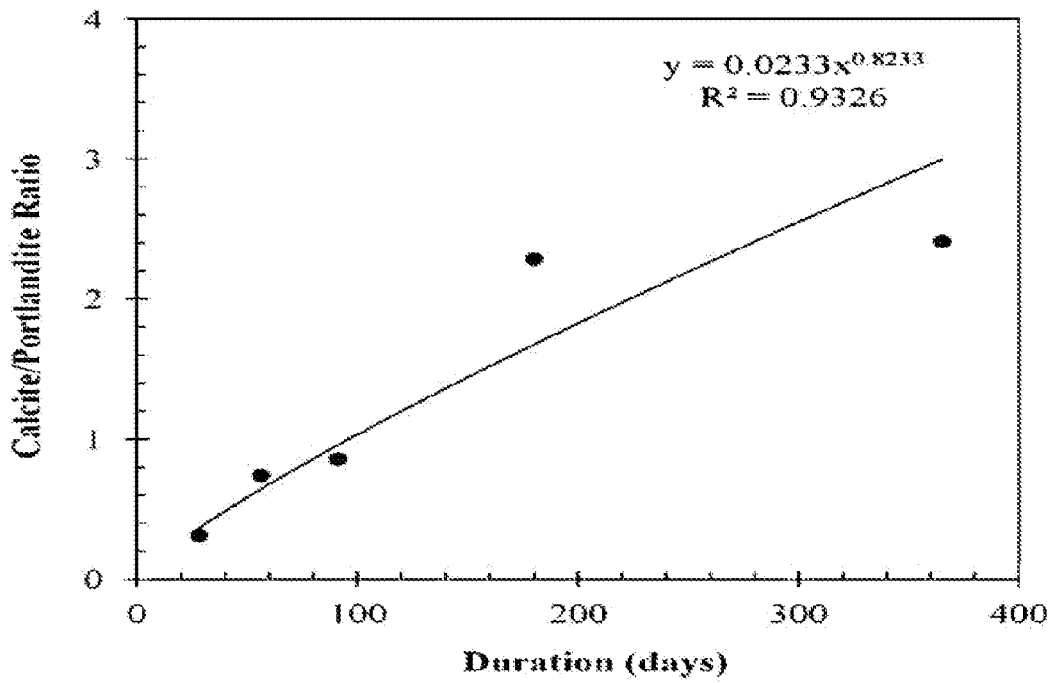
FIG. 20 is a graph illustrating changes in calcite/portlandite ratio according to the exposure time which are analyzed by XRD (FIG. 20: W/B=0.40, FIG. 21: W/B=0.45, and FIG. 22: W/B=0.50)
Figure 21:
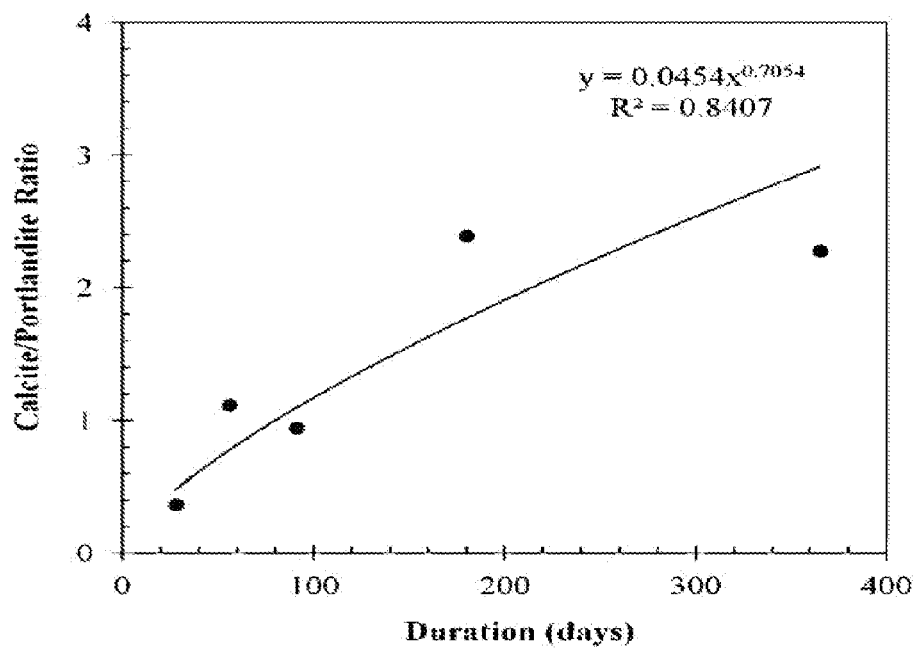
Figure 22:
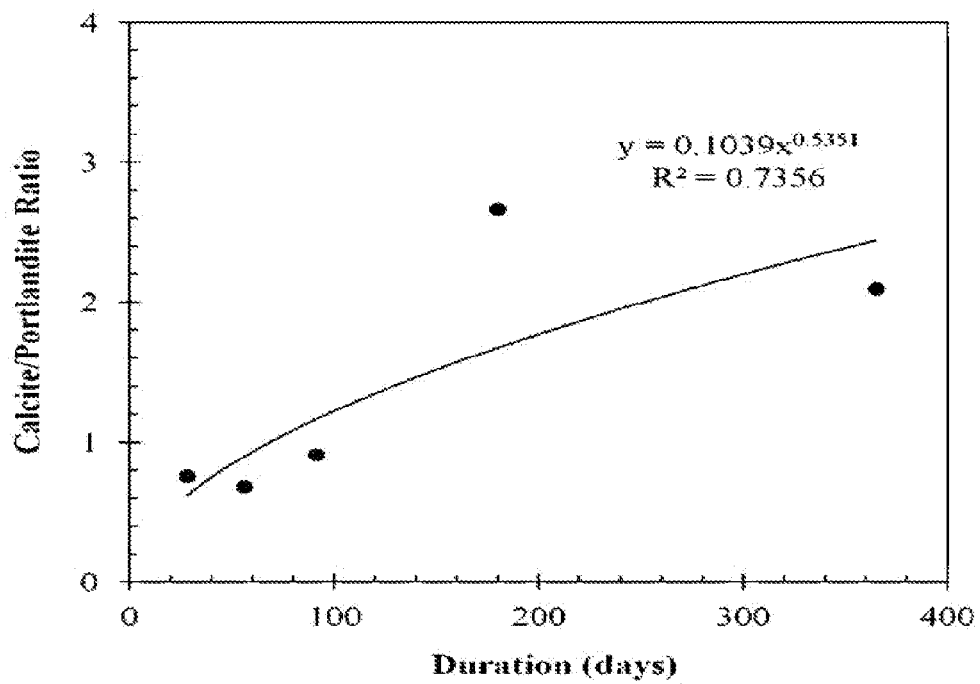

The ratio of calcite/portlandite using the XRD result also showed an increasing tendency similar to the differential thermal gravimetric analysis result, and the ratio of calcite/portlandite exhibited a relatively high coefficient of determination ($R^2$) ranging from 0.74 to 0.93 even though the accuracy of the analysis result was relatively lower than that of the differential thermal gravimetric analysis result as illustrated in FIGS. 20 to 22.

Figure 23:
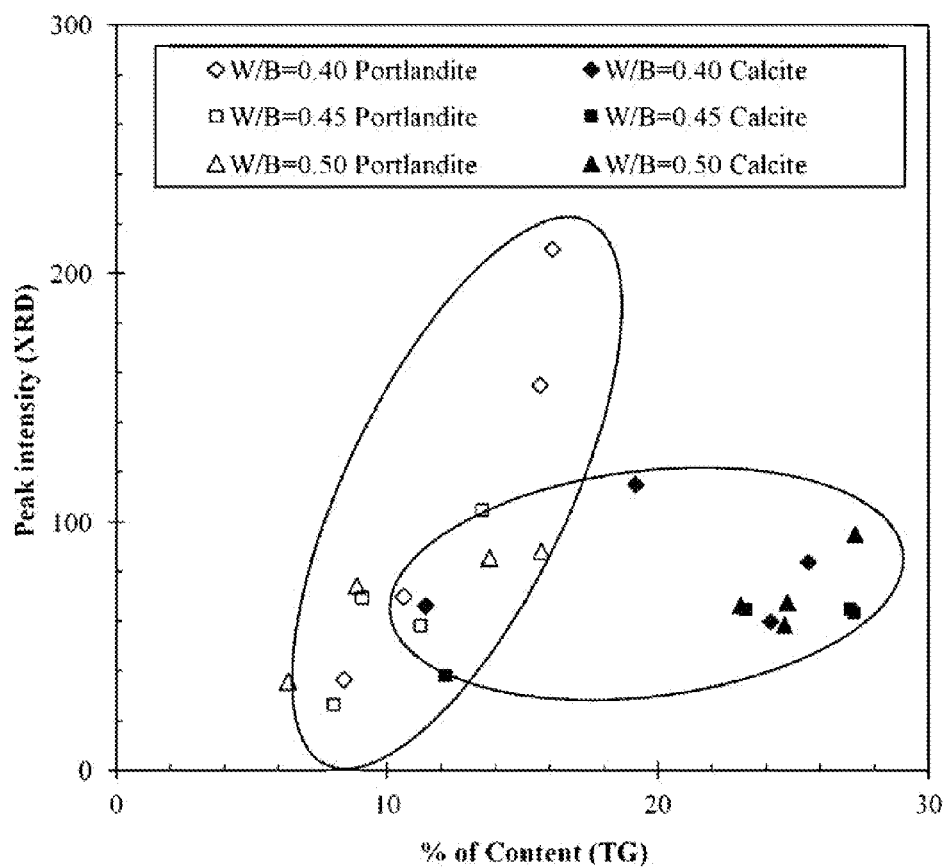
FIG. 23 is a graph illustrating the results of XRD intensity analysis corresponding to the content for each component analyzed by TG-DTA.

In order to investigate the correlation between the results obtained by the differential thermal gravimetric analysis method and the X-ray diffraction method, FIG. 23 illustrates a graph corresponding to the result of each specimen using a content with respect to weight (%) in the case of the differential thermal gravimetric analysis and an intensity in the case of the X-ray diffraction analysis from the analysis result using the same specimen.

However, each corresponding result showed a disordered pattern regardless of the trends according to the water-binder ratio and the exposure time, and it may be confirmed that the portlandite and calcite were also represented as a form in which there was no constant directionality, i.e., it was difficult to find out any trend.

The reason for this is that the X-ray diffraction analysis may exhibit a result having different trend according to the measurement date even if the result was analyzed using the same equipment under the same condition.

Since the result of the X-ray diffraction method had no reliability as described above, the result of the X-ray diffraction method was used only for qualitative and relative comparison.

Figure 24:
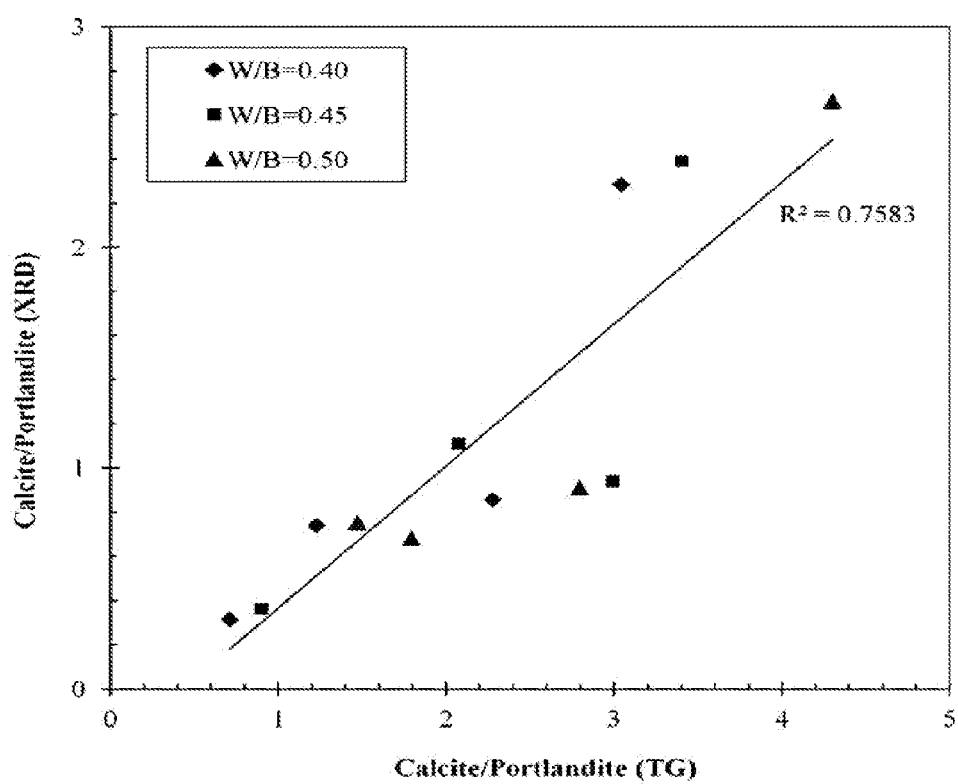
FIG. 24 is a graph illustrating the results of XRD intensity analysis corresponding to the calcite/portlandite ratio analyzed by TG-DTA.

However, in the present invention, the analysis results of the differential thermal gravimetric analysis and X-ray diffraction analysis were illustrated in a graph though the method of evaluating the results using the ratio of calcite/portlandite, and the correlation was examined to illustrate in FIG. 24.

Consequently, the result showed constant directionality according to the water-binder ratio and the exposure time of carbonation, and it may be confirmed that the result showed a constant tendency which had not been confirmed from the simple comparison between the results of the differential thermal gravimetric analysis and X-ray diffraction analysis which are illustrated in FIG. 23.

Also, it may be confirmed that its coefficient of determination ($R^2$) was a relatively high value of 0.76, close to about 0.8.

Accordingly, the accuracy of the a step of converting the first result value A analyzed in the X-ray diffraction analyzing step of the present invention to the second result value B of the differential thermal gravimetric analysis method may be verified.

Also, the accuracy of the b step of calculating the exposure time of carbonation C based on the converted second result value B may be verified.

Thus, according to the method of evaluating concrete carbonation which is provided in the present invention, a semi-quantitative evaluation of concrete carbonation may be possible only by the X-ray diffraction method and analysis results having higher accuracy and reliability may be obtained.

The present invention provides a method of semi-quantitatively evaluating concrete carbonation only by using an X-ray diffraction (XRD) method, which may convert analysis result values of the XRD method to result values of differential thermal gravimetric analysis (TG-DTA) and may calculate the exposure time of concrete carbonation, and an apparatus for semi-quantitatively evaluating concrete carbonation using the same.

While the present invention has been mainly described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. A method of measuring the state of decomposition of a concrete structure by determining the extent of conversion of portlandite to calcite in the structure, comprising:

extracting a specimen taken from the concrete structure to a predetermined depth from the surface of the structure;

dividing the specimen into a plurality of portions from minimum depth to maximum depth; and preparing the specimen portions for x-ray diffraction analysis, said preparation comprises that:

each portion is crushed and combined with water and binder to form a water-binder solution;

the water-binder solution is exposed to carbonation conditions for a plurality of specified time periods;

following the carbonation exposure, the solution is subject to x-ray diffraction analysis that results in a pattern of diffracted x-rays emerging from the solution at various angles;

the diffraction pattern is compared to standard diffraction patterns for portlandite and calcite in which x-rays emerging at a first set of standard diffraction angles indicates the presence of portlandite and x-rays emerging at a second set of standard diffraction angles indicate the presence of calcite;

a ratio of portlandite to calcite is estimated by determining the ratio of intensities of the portlandite specific pattern to the calcite specific pattern to form ratio A;

the x-ray diffraction intensity ratio of converted to a differential thermal gravimetric analysis ratio, B, by use of the formula: $B=1.1784A+0.8704$; and the final ratio of portlandite to carbonate is determined by including the time C, in days, that the sample is exposed to carbonation using the formula: $C=8.62B^{2.89}$.

2. A method of measuring the state of decomposition of a concrete structure by determining the extent of conversion of portlandite to calcite in the structure, comprising:

extracting a specimen taken from the concrete structure to a predetermined depth from the surface of the structure;

dividing the specimen into a plurality of portions from minimum depth to maximum depth; and preparing the specimen portions for x-ray diffraction analysis, said preparation comprises that:

each portion is crushed and combined with water and binder to form a water-binder solution;

the water-binder solution is exposed to carbonation conditions for a plurality of specified time periods;

following the carbonation exposure, the solution is subject to x-ray diffraction analysis that results in a pattern of diffracted x-rays emerging from the solution at various angles;

the diffraction pattern is compared to standard diffraction patterns for portlandite and calcite in which x-rays emerging at a first set of standard diffraction angles indicates the presence of portlandite and x-rays emerging at a second set of standard diffraction angles indicate the presence of calcite;

a ratio of portlandite to calcite is estimated by determining the ratio of intensities of the portlandite specific pattern to the calcite specific pattern to form ratio A; and the x-ray diffraction intensity ratio of converted to a differential thermal gravimetric analysis ratio, B, by use of the formula: $B=1.1784A+0.8704$.

* * * * *